US006322571B1

(12) United States Patent
Adams

(10) Patent No.: US 6,322,571 B1
(45) Date of Patent: Nov. 27, 2001

(54) APPARATUS AND METHOD FOR PLACING SUTURES IN THE LACERATED END OF A TENDON AND SIMILAR BODY TISSUES

(76) Inventor: Brian D. Adams, 3673 Forest Gate Dr., NE., Iowa City, IA (US) 52240

( * ) Notice: Subject to any disclaimer, the term of this patent is extended or adjusted under 35 U.S.C. 154(b) by 0 days.

(21) Appl. No.: 09/286,198

(22) Filed: Apr. 5, 1999

Related U.S. Application Data
(60) Provisional application No. 60/088,153, filed on Jun. 5, 1998.

(51) Int. Cl.⁷ .................................................. A61B 17/04
(52) U.S. Cl. ........................ 606/151; 606/148; 606/144; 606/207
(58) Field of Search ..................................... 609/151, 139, 609/160, 148, 153, 157, 158; 623/11, 12, 13, 14, 15, 16

(56) References Cited

U.S. PATENT DOCUMENTS

| 963,899 | * | 7/1910 | Kistler .................................. 606/148 |
| 3,176,316 | | 4/1965 | Bodell ........................................... 3/1 |
| 3,545,008 | | 12/1970 | Bader, Jr. ..................................... 3/1 |
| 3,633,582 | | 1/1972 | Steinman ............................. 128/334 |
| 3,745,590 | | 7/1973 | Stubstad . |
| 4,469,101 | | 9/1984 | Coleman et al. ............................ 3/1 |
| 4,553,543 | | 11/1985 | Amarasinghe ................... 128/334 R |
| 4,585,458 | | 4/1986 | Kurland ................................. 623/13 |
| 4,602,634 | | 7/1986 | Barkley ................................ 128/334 |

(List continued on next page.)

FOREIGN PATENT DOCUMENTS

| 0 820 725 A2 | 1/1998 | (EP) .............................. A61B/17/11 |
| WO 96/16612 | 6/1996 | (WO) ................................ A61F/2/08 |
| 97/37002 | 10/1997 | (WO) .............................. C12N/5/06 |

OTHER PUBLICATIONS

International Preliminary Examination Report for pending application PCT/US99/23491, Apr. 6, 2001.
"The Pactan Repair Device," Small Joint Orthopaedics, by Wright Medical Technology, Inc.
"Plastic & Reconstructive/Hand Surgery" by Accurate Surgical & Scientific Instruments Corp.
International Search Report for PCT/US99/11821 mailed Sep. 6, 1999, 7 pages.
"Goldstein Microspike, Approximator Clamps fr Vasovasostomy & Vasoepididymostomy," Accurate Surgical & Scientific Instruments Corporation.
"Surgery of Peripheral Nerves and Tendons" by V.E. Meyer, S&T Marketing Ltd.
"Flexor Tendon Injuries: I. Foundations of Treatment" by James W. Strickland, M.D., Journal of the American Academy of Orthopaedic Surgeons, vol. 3, #1, Jan./Feb. 1995.
"Flexor Tendon Injuries: II. Operative Technique" by James W. Strickland, M.D., Journal of the American Academy of Orthopaedic Surgeons, vol. 3, #1, Jan./Feb. 1995.
International Search Report for PCT/US 99/23491, Feb. 1, 2000.

Primary Examiner—David O. Reip
(74) Attorney, Agent, or Firm—Baker Botts L.L.P.

(57) ABSTRACT

A suture repair system is provided for releasably holding the lacerated end of a tendon, ligament, and similar types of body tissues and precisely guiding placement of one or more sutures therein. The suture repair system preferably provides one or more suture guide paths for placing respective sutures having a selected configuration in the lacerated end. The system preferably includes a single use, disposable holder or clamp assembly. The clamp assembly may also be used as a guide to accurately trim, when necessary, the lacerated end. Once suture placement is completed the clamp assembly may be removed and may be discarded.

20 Claims, 3 Drawing Sheets

U.S. PATENT DOCUMENTS

| | | | |
|---|---|---|---|
| 4,635,636 | 1/1987 | Goldstein | 128/334 |
| 4,723,548 | 2/1988 | Lalonde | 128/335 |
| 4,960,420 | 10/1990 | Goble et al. | 606/72 |
| 5,007,920 | 4/1991 | Torre | 606/207 |
| 5,251,642 * | 10/1993 | Handlos | 128/77 |
| 5,298,012 | 3/1994 | Handlos | 600/36 |
| 5,366,457 | 11/1994 | McGuire et al. | 606/86 |
| 5,415,651 | 5/1995 | Schmieding | 606/1 |
| 5,464,415 | 11/1995 | Chen | 606/153 |
| 5,534,008 * | 7/1996 | Acksel | 606/148 |
| 5,593,024 | 1/1997 | Seiler | 206/5 |
| 5,624,453 | 4/1997 | Ahmed | 606/140 |
| 5,649,937 | 7/1997 | Bito et al. | 606/139 |
| 5,656,605 | 8/1997 | Hansson et al. | 514/21 |
| 5,697,933 * | 12/1997 | Gundlapalli et al. | 606/96 |
| 5,746,757 * | 5/1998 | McGuire | 606/148 |
| 5,800,544 | 9/1998 | Demopoulos et al. | 623/13 |
| 5,843,098 * | 12/1998 | Allen et al. | 606/144 |

\* cited by examiner

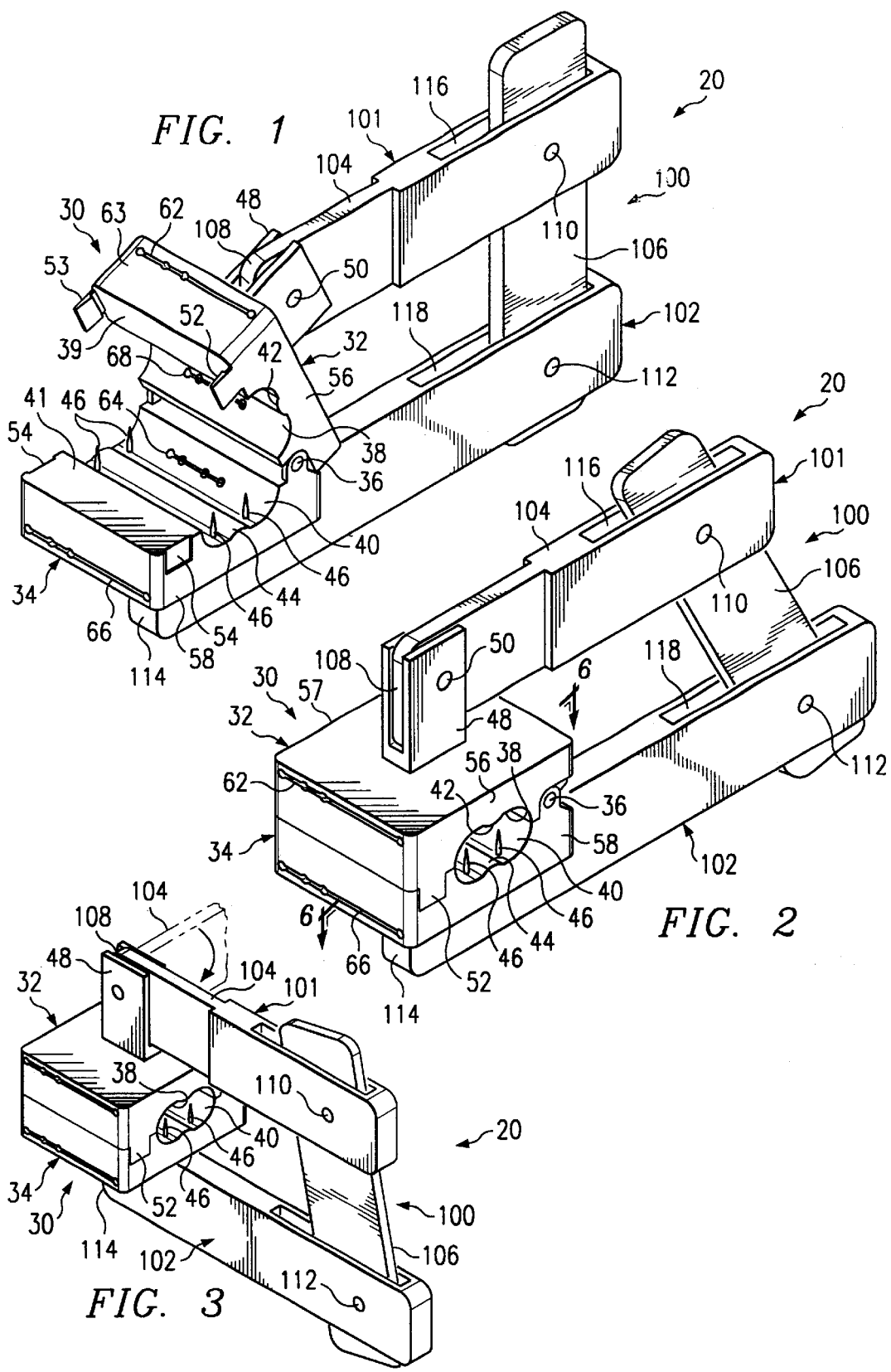

APPARATUS AND METHOD FOR PLACING SUTURES IN THE LACERATED END OF A TENDON AND SIMILAR BODY TISSUES

RELATED APPLICATIONS

This application claims the benefit of U.S. Provisional Application Serial No. 60/088,153 filed Jun. 5, 1998 entitled Tendon Suture-Repair Device and Method.

This application is related to copending U.S. patent application Ser. No. 60/111,490 filed Dec. 8, 1998 entitled Tendon Passing Device and Method.

TECHNICAL FIELD OF THE INVENTION

The invention relates generally to medical devices and more particularly to apparatus and methods for repairing a divided or ruptured tendon, ligament and other fibrous body tissues using a suture.

BACKGROUND OF THE INVENTION

A wide variety of equipment and procedures have previously been used to perform tenorrhaphy, the union of a divided or ruptured tendon by a suture and tenodesis, the suturing of the end of a tendon to a bone. Over the past decade, several multiple grasping, multiple strand suture techniques have been developed to repair tendon lacerations. These techniques are based on the concept that repair strength is roughly proportional to the number of suture strands that cross the repair site. In addition, suturing techniques that appropriately grasp a tendon at multiple sites generally create a stronger repair than a simple weave.

Although these repair techniques provide greater strength, their use has not been widespread because they are technically quite demanding. In fact, even traditional methods of tendon repair are difficult to satisfactorily perform due to the small size and other characteristics of tendons and the correspondingly small surgical field. The technique of tendon repair has become an even greater concern due to demands placed on such repairs by aggressive rehabilitation. Thus, surgeons face the dilemma of using stronger suture techniques to improve outcome but which are also much more difficult and time-consuming to perform and may possibly cause additional damage to the tendon.

During tendon repair, it is important to minimize any further damage to a lacerated tendon. The lacerated ends of a tendon tend to fray when handled, especially when an attempt is made to place multiple sutures in the lacerated end of the tendon. In addition, surgical trauma increases postoperative adhesions possibly resulting in decreased digital motion which is undesirable.

SUMMARY OF THE INVENTION

Accordingly, a need has arisen for improved equipment and methods to place multiple sutures in the lacerated end of a tendon, ligament or other types of fibrous body tissues. One aspect of the present invention includes a tendon suture-repair device having a clamp assembly for securely holding the lacerated end of a tendon and guiding suture placement in the lacerated end. Another aspect of the present invention includes providing a clamp assembly having a cutting guide to allow easy and neat trimming of the lacerated end of a tendon or ligament prior to placement of one or more sutures therein. A manipulator is preferably provided for opening and closing the clamp assembly and positioning the clamp assembly with the lacerated end disposed therein during surgical repair.

According to one embodiment of the invention, a repair technique and device are provided to efficiently produce a high quality multiple grasping, multiple strand suture repair of a lacerated tendon. The device achieves the advantages of such repair while eliminating most of the frustration associated with traditional tendon suturing techniques. In addition, the device greatly reduces unwanted and deleterious handling of a tendon to substantially mitigate surgical trauma which often occurs with the use of standard surgical instruments.

Technical benefits of the present invention include tendon repair procedures and equipment satisfactory for use with contemporary surgical practices and rehabilitation programs. The relatively small size and configuration of equipment incorporating teachings of the present invention is compatible with relatively small surgical fields commonly associated with tendon and ligament repair. Additional technical benefits include providing generally a stronger tendon repair as compared to traditional tenorrhaphy equipment and procedures. The resulting tendon repair will generally meet or exceed the standards of contemporary surgery and rehabilitation for tendon injuries. More aggressive rehabilitation programs have demonstrated improved clinical results for patients having a lacerated tendon. Repairing a tendon using apparatus and methods incorporating teachings of the present invention will often allow patients to better participate in such rehabilitation programs.

Another aspect of the present invention includes providing apparatus and methods which may be used to repair lacerated tendons or ligaments in a patient's upper and lower extremities and for suturing the end of a tendon to a bone. One embodiment of the present invention includes a clamp assembly having a channel formed therein to securely but gently hold the lacerated end of a tendon and substantially reduce or eliminate deleterious effects of handling the tendon during placement of sutures. The size and shape of a clamp assembly and associated components may be selected in accordance with the teachings of the present invention to accommodate restrictions imposed by relatively small operating fields available during tendon repair surgery. A tendon repair system incorporating teachings of the present invention is generally more accurate and efficient as compared to previous techniques and provides more uniform, reproducible results from one surgical procedure to the next.

Equipment and procedures incorporating teachings of the present invention may be used by all surgeons as well as any physician who performs tendon and ligament repairs, including emergency room (ER) physicians. In addition, such equipment and procedures may be used for tendon or ligament transfer and operations that use body tissue grafts such as a ligament reconstruction in the hand or foot.

BRIEF DESCRIPTION OF THE DRAWINGS

For a more complete understanding of the present invention, and the advantages thereof, reference is now made to the following brief descriptions, taken in conjunction with the accompanying drawings and detailed description, wherein like reference numerals represent like parts, in which:

FIG. 1 is a schematic drawing showing an isometric view of a tendon repair system incorporating teachings of the present invention including a tendon holder or clamp assembly in its first, open position and an associated manipulator in its first position;

FIG. 2 is a schematic drawing showing an isometric view of the tendon repair system of FIG. 1 with the clamp assembly in its second, closed position and the manipulator in its second position;

FIG. 3 is a schematic drawing showing an isometric view of the tendon repair system of FIG. 1 with the clamp assembly in its second, closed position and the manipulator in its third position;

DETAILED DESCRIPTION OF THE INVENTION

Preferred embodiments of the present invention and its advantages are best understood by referring now in more detail to FIGS. 1–7 of the drawings, in which like numerals refer to like parts.

Figure 4A:
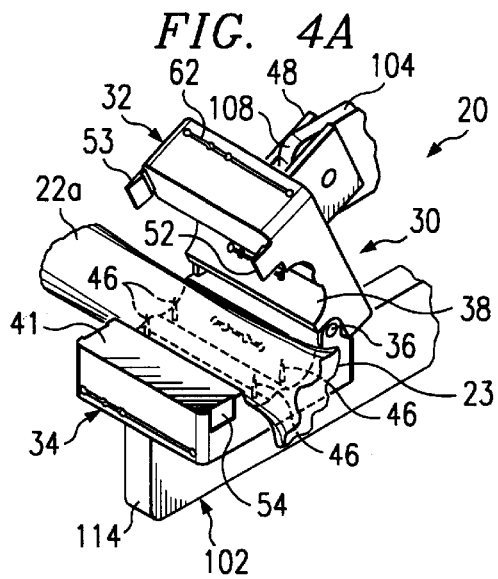
FIG. 4A is a schematic drawing showing an isometric view with portions broken away of the clamp assembly of FIG. 1 in its first, open position and the lacerated end of a tendon disposed therein.
Figure 4B:
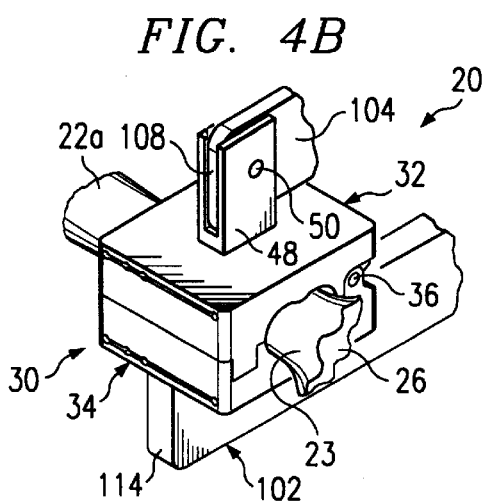
FIG. 4B is a schematic drawing showing an isometric view with portions broken away of the clamp assembly of FIG. 1 in its second position, closed with the lacerated end of the tendon firmly secured therein.
Figure 4C:
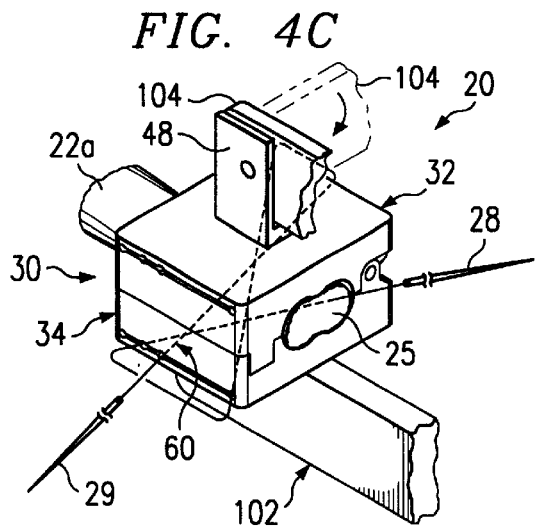
FIG. 4C is a schematic drawing showing an isometric view with portions broken away of a suture being inserted through the lacerated end of the tendon in accordance with teachings of the present invention.
Figure 4D:
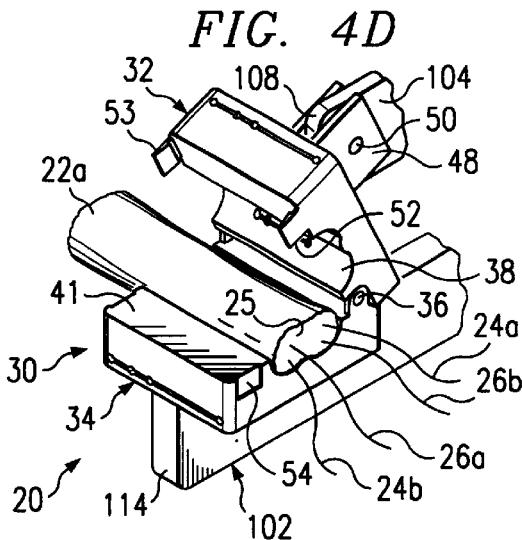
FIG. 4D is a schematic drawing showing an isometric view with portions broken away of the clamp assembly of FIG. 1 in its first, open position with sutures disposed in the lacerated end of the tendon in accordance with teachings of the present invention.
Figure 5:
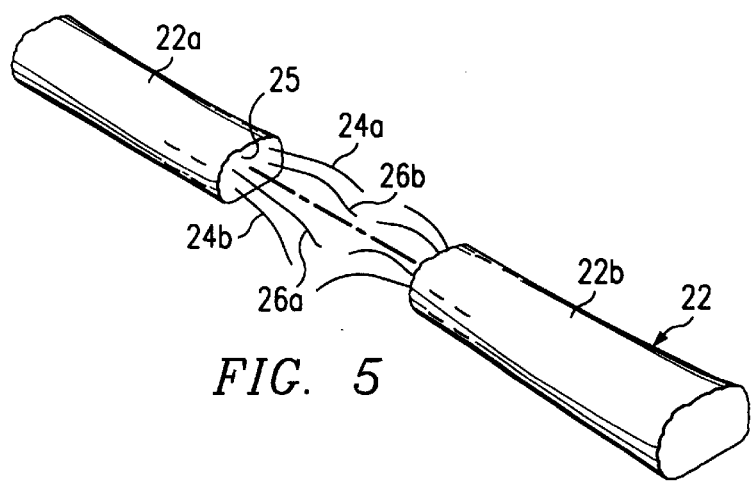
FIG. 5 is a schematic drawing showing an isometric view with portions broken away of adjacent lacerated ends of a tendon having sutures inserted therein using apparatus and techniques incorporating teachings of the present invention.

For purposes of explaining various teachings of the present invention, tendon repair system 20 as shown in FIGS. 1, 2, 3, 4A–D, 6 and 7 will be described with respect to repairing lacerated tendon 22 portions of which are shown in FIG. 5.

Tendons may be generally described as fibrous cords (not expressly shown) or bands of body tissue which connect associated muscles (not expressly shown)to a (not expressly shown) bone. Ligaments may be described as fibrous cords (not expressly shown) or bands of body tissue which connect bones or cartilages with each other to support and strengthen an associated joint (not expressly shown). Tendons and ligaments are generally composed of multiple collagen bundles and as a result have some of the characteristics associated with a braided rope (including the tendency to fray).

The term "lacerated" is used to describe tendons, ligaments and similar types of fibrous body tissue which have been cut, torn, ripped or ruptured.

The ends of a lacerated tendon or ligament have a tendency to fray during manipulation while performing surgical repairs. Apparatus and methods incorporating teachings of the present invention may be satisfactorily used to repair lacerated tendons, ligaments and similar types of fibrous body tissue while minimizing surgical trauma.

Tendon repair system 20 preferably includes clamp assembly 30 with manipulator 100 attached thereto. Clamp assembly 30 may sometimes be referred to as an "enclosure" or as a "tendon holder." Various types of enclosures and tendon holders other than clamp assembly 30 may be formed in accordance with teachings of the present invention to releasably hold a lacerated tendon or ligament. Clamp assembly 30 and manipulator 100 may sometimes be referred to as a "tendon suture-repair device." The present invention is not limited to clamp assembly 30 or manipulator 100. A wide variety of clamp assemblies and manipulators may be formed in accordance with teachings of the present invention for use in repairing lacerated tendons, ligaments and similar types of fibrous body tissue.

For the embodiment of the present invention as shown in FIGS. 1, 2, 3, 4A–D, 6 and 7, clamp assembly 30 preferably includes a pair of jaws 32 and 34. Active hinge 36 is coupled with first jaw 32 and second jaw 34 extending longitudinally along one side of clamp assembly 30. Manipulator 100 may be used to open and close clamp assembly 30 to allow insertion and removal of lacerated end 22a of tendon 22 as illustrated in FIGS. 4A–D.

For one embodiment of the present invention, jaws 32 and 34 may have generally similar box type configurations which cooperate with each other to form an enclosure for releasably holding the lacerated end of a tendon or ligament and for guiding placement of one or more sutures therein. When clamp assembly 30 is in its second, closed position, the resulting rectangular box type enclosure for this embodiment may have a length (L) of approximately eleven millimeters, a width (W) of approximately thirteen millimeters and a height (H) of approximately seven millimeters (11 mm×13 mm×7 mm). See FIG. 7.

Channels 38 and 40 are respectively disposed in and extend longitudinally through surfaces 39 and 41 of jaws 32 and 34. Channels 38 and 40 are aligned generally parallel with hinge 36. The dimensions and configurations of channels 38 and 40 are preferably selected to accommodate placing the lacerated end of a typical flexor tendon therein.

For purposes of describing various features of the present invention, the terms "longitudinal" and "longitudinally" will be used to describe a direction corresponding generally with the direction in which channels 38 and 40 extend through clamp assembly 30. The terms "lateral" and "laterally" will be used to describe a direction which is generally normal to channels 38 and 40 and parallel with surfaces 39 and 41 when clamp assembly 30 is in its second, closed position.

When clamp assembly 30 is in its first, open position as shown in FIGS. 1, 4A and 4D, surface 39 of first jaw 32 will be spaced from surface 41 of second jaw 34. When clamp assembly 30 is in its second, closed position, such as shown in FIGS. 2, 3, 4B, 4C and 7, surface 39 of jaw 32 will be in close, intimate contact with surface 41 of jaw 34.

For some applications such as shown in FIGS. 1–4D, a pair of flexible collets or snaps 52 may be formed on opposite ends of first jaw 32 extending therefrom. A pair of corresponding recesses may also be formed on opposite ends of second jaw 34. One such recess 54 is shown in FIGS. 1, 4A and 4D. Flexible collets or snaps 52 and 53 are preferably aligned with and sized to be received within respective recesses 54 when clamp assembly 30 is in its second, closed position such as shown in FIGS. 2 and 3. Flexible collets 52 and 53 and respective recesses 54 cooperate with each other to provide a locking mechanism for releasably holding clamp assembly 30 in its second, closed position when the lacerated end of a tendon or ligament is secured therein.

Manipulator 100 and hinge 36 cooperate with each other to allow movement of clamp assembly 30 between its first, open position as shown in FIG. 1 and its second, closed position as shown in FIG. 2. Manipulator 100 also allows a surgeon to comfortably hold clamp assembly 30 when the lacerated end of a tendon or ligament is disposed therein and to position clamp assembly 30 to facilitate placement of sutures in the lacerated end of the tendon or ligament.

Schematic representations of portions of lacerated tendon 22 are shown in FIGS. 4A–D, 5 and 6. Tendon 22 may be described as a typical flexor tendon which generally have oval shaped cross-sections varying in size from approximately five millimeters by two millimeters to eight millimeters by three millimeters. An average flexor tendon has an oval shaped cross-section of approximately six millimeters by two millimeters.

Each channel 38 and 40 preferably has a crosssection corresponding approximately with one-half of an oval. For one application, channels 38 and 40 have a length of approximately one-half an inch or eleven millimeters and a width of approximately 0.282 inches or six millimeters. The depth of each channel 38 and 40 within its respective jaw 32 and 34 is approximately 0.06 inches or one millimeter. When clamp assembly 30 is in its second, closed position, channels 38 and 40 cooperate with each other to form a generally oval shaped passageway extending longitudinally through clamp assembly 30. The resulting generally oval shaped passageway will have a width of approximately six millimeters and a height of approximately two millimeters.

The dimensions and configuration of clamp assembly 30 are selected to accommodate restrictions associated with relatively small operating fields available during tendon repair surgery. The dimensions and configuration of channels 38 and 40 are also selected to firmly but gently hold the lacerated end of a tendon therein.

For some applications such as shown in FIGS. 1–4D and FIG. 6, channels 38 and 40 may also include respective ribs or protrusions 42 and 44 extending therefrom along the length thereof. Ribs 42 and 44 are preferably aligned parallel with the longitudinal centerline (not expressly shown) of respective channels 38 and 40. For one application, ribs 42 and 44 may extend approximately 0.2 millimeters into the respective channels 38 and 40. Ribs 42 and 44 cooperate with other portions of channels 38 and 40 to gently but firmly secure the lacerated end of a tendon or ligament within clamp assembly 30.

As shown in FIGS. 2 and 3 the cross section of the resulting passageway extending through clamp assembly 30 may be described as a modified oval having a configuration similar to a "peanut" when clamp assembly 30 is in its second, closed position. The longitudinal opening extending through clamp assembly 30 may also be described as being divided into quadrants defined in part by ribs 42 and 44 and the junction between surface 39 of first jaw 32 with surface 41 of second jaw 34. As discussed later in more detail, clamp assembly 30 preferably includes one or more suture guide paths to facilitate placing a suture strand extending from the lacerated end of a tendon or ligament at a location corresponding with each quadrant of the longitudinal passageway formed in clamp assembly 30. See FIGS. 4D and 5.

For the embodiment of the present invention as shown in FIGS. 1, 2, 3, 4A, and 6, a plurality of spikes 46 may be disposed within channel 40 of second jaw 34 to engage lacerated end 22a of tendon 22. See FIG. 4A. The number of spikes and their configuration, dimensions and location may be varied depending upon the size and type of fibrous body tissue which will be releasably secured within the associated clamp assembly. The dimensions and configuration of channels 38 and 40 in cooperation with spikes 46 may be selected to substantially minimize any damage which may result from handling lacerated end 22a of tendon 22 during placement of sutures 24 and 26 therein. The present invention is not limited to channels and spikes having configurations and dimensions as described in this application. For some surgical procedures and/or types of fibrous body tissues spikes 46 may not be required.

For the embodiment of the present invention as shown in FIGS. 1–4D, manipulator 100 includes first arm 101 and second arm 102. First arm 101 preferably includes first segment 104 and second segment 106 which are rotatably attached to each other by pin 110. First arm 101 may be described as an "articulated arm." End 108 of first segment 104 is preferably attached to bracket 48 extending from first jaw 32.

For the embodiment of the present invention as shown in FIGS. 1–4D and FIG. 7, bracket 48 has a generally U-shaped configuration. Brackets with other configurations may be satisfactorily used with the present invention. End 108 of first segment 104 of arm 101 is preferably disposed within bracket 48 with pin 50 extending therethrough. The dimensions of bracket 48, pin 50 and end 108 of first segment 104 are preferably selected to allow limited rotation of first segment 104 relative to bracket 48 during opening and closing of clamp assembly 30.

Second segment 106 of first arm 101 preferably extends between first segment 104 and second arm 102. For the embodiment of the present invention as shown in FIGS. 1, 2 and 3, pin 110 extends through respective portions of first segment 104 and second segment 106. A similar pin 112 extends through respective portions of second segment 106 and second arm 102. Pins 110 and 112 cooperate with each other to allow rotation of first segment 104 and second segment 106 of first arm 101 relative to each other and relative to second arm 102 during opening and closing of clamp assembly 30.

Bracket 48 is preferably attached to first jaw 32 by a pivotal type connection (not expressly shown). End 114 of second arm 102 is also preferably pivotally attached (not expressly shown) with second jaw 34. As a result of respective pivotal connections between bracket 48 and first jaw 32 and between end 114 of second arm 102 and second jaw 34, manipulator 100 may rotate from a position extending approximately normal to channels 38 and 40 such as shown in FIGS. 1 and 2 to a second position aligned generally parallel with channels 38 and 40 as shown in FIG. 3 and 4C.

Manipulator 100 has a first position corresponding with the first, open position of clamp assembly 30 as shown in FIG. 1. Manipulator 100 has a second position as shown in FIG. 2 corresponding with the second, closed position of clamp assembly 30. Manipulator 100 preferably extends generally normal to channels 38 and 40 in both its first and second positions. Manipulator 100 may also be placed in a third position as shown in FIG. 3 with arms 101 and 102 aligned generally parallel with channels 38 and 40. Manipulator 100 is preferably placed in its third position to accommodate placing sutures 24 and 26 in end 22a of lacerated 22. See FIGS. 4C and 4D.

Respective portions of second segment 106 of first arm 101 are respectively disposed within slot 116 of first segment 104 and slot 118 of second arm 102. The dimensions and configuration of slots 116 and 118 in cooperation with the dimensions and configuration of second segment 106 are selected to provide mechanical stops or limits which prevent excessive movement of first arm 101 and second arm 102 relative to each other during opening and closing of clamp assembly 30. Such stops cooperate with each other to prevent jamming of clamp assembly 30 and/or manipulator 100.

The dimensions and configuration of first arm 101 and second arm 102 are preferably selected to accommodate holding manipulator 100 between the index finger (not expressly shown) and thumb (not expressly shown) of a surgeon while opening and closing clamp assembly 30.

First arm 101 may be manipulated with a surgeon's thumb to open and close clamp assembly 30. When clamp assembly 30 is in its closed position as shown in FIG. 4B, manipulator 100 may be held between the tips of the surgeon's index finger and thumb to move manipulator 100 to its third position as shown in FIGS. 4C.

Figure 6:
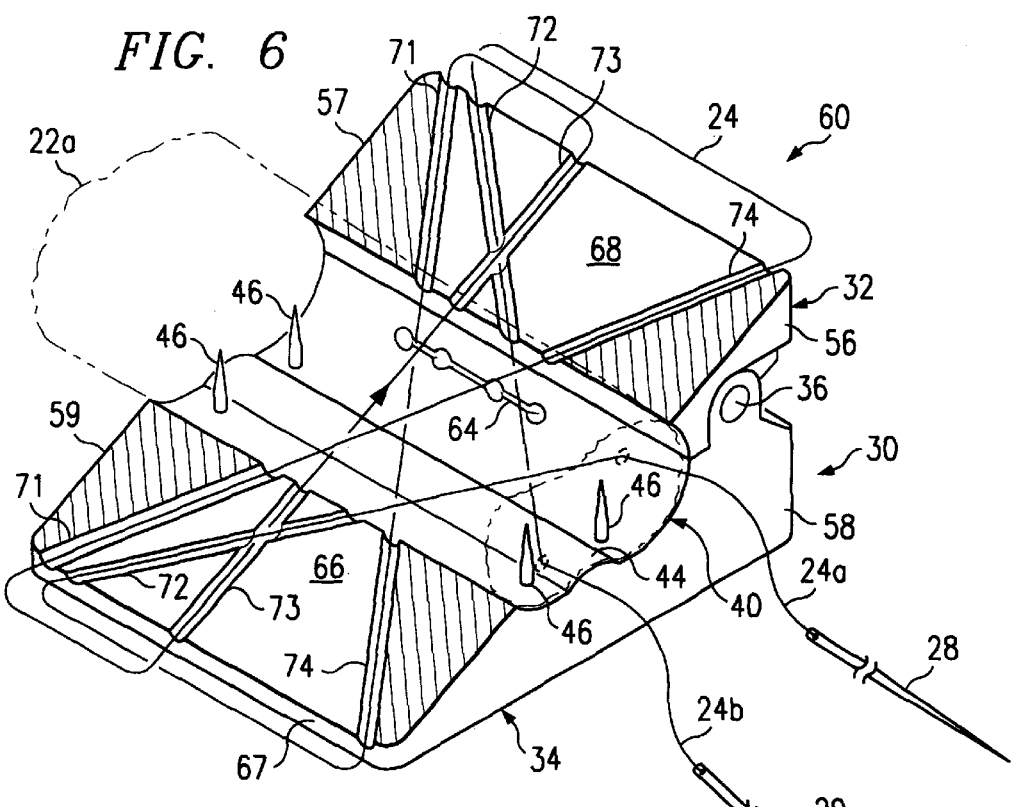
FIG. 6 is a schematic drawing showing an isometric view, partially in section with portions broken away, of one pattern for inserting sutures through the lacerated end of a tendon disposed within a clamp assembly in accordance with teachings of the present invention.

A clamp assembly incorporating teachings of the present invention will preferably include at least one suture guide path for use in placing one or more sutures in the lacerated end of a tendon or ligament. For the embodiment of the present invention as shown in FIGS. 1 through 4D, 6 and 7, clamp assembly 30 preferably includes two separate suture guide paths which allow placement of sutures 24 and 26 in lacerated ends 22a and 22b of tendon 22. One of the suture guide paths formed in clamp assembly 30, designated as guide path 60, is shown in FIG. 6. Portions of the other suture guide path are also shown in FIGS. 1–4D, 6 and 7. As discussed later in more detail, clamp assembly 30 facilitates placement of suture strands 24a, 24b, 26a and 26b within and extending longitudinally from lacerated end 22a and 22b of tendon 22 as shown in FIG. 5.

The first suture guide path is defined in part by slot 62 which extends from exterior surface 63 of first jaw 32 and intersects with channel 38. The first guide path also includes a corresponding slot 64 formed in second jaw 34 extending from channel 40 to the exterior thereof. Slots 62 and 64 are preferably aligned with each other in the same plane.

Second suture guide path 60 provided in clamp assembly 30 is defined in part by slot 66 formed in second jaw 34 extending from exterior surface 67 to channel 40. Second suture guide path 60 is also defined in part by slot 68 formed in first jaw 32 extending from channel 38 to the exterior thereof. As best shown in FIG. 6, slots 66 and 68 have a generally trapezoidal configuration and are preferably aligned with each other Slots 62, 64, 66 and 68 cooperate with each other to expose selected portions of the exterior surface of lacerated ends 22a and 22b of tendon 22 for placement of respective sutures 24 and 26 therein.

For the embodiment of the present invention as represented by clamp assembly 30, slots 62, 64, 66 and 68 preferably have substantially the same generally trapezoidal configuration and dimensions. For other applications, slots with different sizes and configuration may be satisfactorily used with clamp assembly 30.

Figure 7:
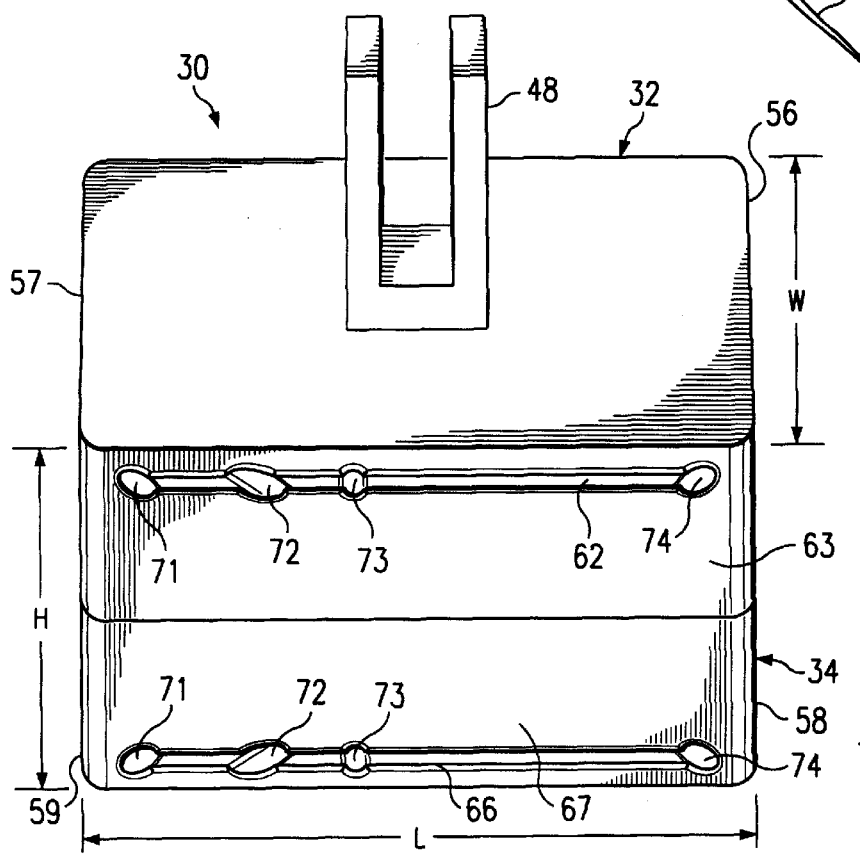
FIG. 7 is a schematic drawing in elevation showing another view of the clamp assembly of FIG. 1 in its closed position.

Slot 62, 64, 66, and 68 preferably have a width corresponding approximately with the thickness or diameter of the type of suture selected for placement in the lacerated end of a tendon or ligament but smaller than the diameter of needles attached to the suture. For the embodiment of the present invention as shown in FIGS. 6 and 7, slots 62, 64, 66 and 68 allow passage of suture 24 but not needles 28 and 29. Slots 62, 64, 66 and 68 will preferably have a width of approximately 0.125 millimeters when clamp assembly 30 is used to place type 4-0 sutures in lacerated ends 22a and 22b of tendon 22. Other sutures such as type 3-0 may also be satisfactorily used with the present invention.

Each slot 62, 64, 66 and 68 preferably extends at an angle of approximately twenty-two and a half degrees (22½) relative to surfaces 39 and 41 of jaws 32 and 34 and the associated longitudinal axis of channels 38 and 40. The first suture guide path defined in part by slots 62 and 64 and second suture guide path 60 defined in part by slots 66 and 68 preferably intersect with each other at an angle of approximately forty-five degrees extending along the longitudinal center line (not expressly shown) of clamp assembly 30.

For some tendon and/or ligament repairs a clamp assembly may be formed with only one suture guide path or may be formed with two or more suture guide paths which intersect each other at angles other than forty-five degrees. One of the technical benefits of the present invention includes the ability to vary the number and location of sutures placed within the lacerated end of a tendon, ligament or similar type of fibrous body tissue as desired to improve the results of the associated surgical procedure and rehabilitation.

Each slot 62, 64, 66 and 68 preferably includes four enlargements or holes 71, 72, 73 and 74 formed therein and extending therethrough. The diameter of holes 71, 72, 73 and 74 preferably corresponds with the width or diameter of needles used with the selected suture. For the embodiment of the present invention a shown in FIGS. 6 and 7, holes 71, 72, 73 and 74 guide needles 28 and 29 through lacerated ends 22a and 22b of tendon 22. For type 4-0 sutures, the associated needles will typically have a width of approximately 0.4 millimeters.

For the embodiment of the present invention as best shown in FIG. 6, holes 73 are disposed in respective slots 66 and 68 aligned with each other and extending generally perpendicular to channels 38 and 40. Hole 71 in slot 66 is preferably aligned with hole 74 in slot 68. Hole 71 in slot 68 is preferably aligned with hole 74 in slot 66. Holes 71 and 74 extend at a first angle relative to channels 38 and 40.

Hole 72 in slot 66 preferably extends at a second angle from the exterior of second jaw 34 to a selected quadrant in the opening defined by channels 38 and 40 at end 56 of first jaw 32. Hole 72 in slot 68 preferably extends at an angle from the exterior of first jaw 32 to a selected quadrant in the opening defined by channels 38 and 40 at end 58 of second jaw 34. Holes 71, 72, 73 and 74 cooperate with each other to guide placement of respective sutures 24 and 26 within lacerated ends 22a and 22b of tendon 22 such that respective suture strands 24a, 24b, 26a and 26b will extend from opposite quadrants thereof. See FIG. 5.

Holes 71, 72, 73 and 74 formed in slots 62 and 64 have similar orientations with respect to channels 38 and 40 as previously described with respect to slots 66 and 68. As a result of the suture guide paths formed in clamp assembly 30, sutures 24 and 26 will each grasp lacerated end 22a twice on opposite sides thereof. Thus, suture 24 will grasp the exterior of lacerated end 22a of tendon 24 four times as shown in FIG. 5. In a similar manner, suture 26 will also grasp the exterior of lacerated end 22a of tendon 22 in four separate locations on the exterior thereof.

The length of the grasp of the sutures on the exterior of lacerated end 22a is determined by the spacing between the intersection of holes 71 and 73 with respective channels 38 and 40 and the intersection of holes 72 and 74 with respective channels 38 and 40. For one embodiment of the present invention, the length of each grasp on the exterior of lacerated end 22a of tendon 22 will measure approximately one and one-half millimeters.

The present invention is not limited to a suture guide path having holes 71, 72, 73 and 74. Various configurations and combinations of holes and slots may be satisfactorily used to provide a suture guide path in accordance with teachings of the present invention.

Tendon and ligament repairs are often conducted in relatively small surgical fields due to the limited amount of exposure typically available at the lacerated end of a tendon or ligament. The relatively small size and configuration of clamp assembly 30 and manipulator 100 allow tendon repair system 20 to releasably engage only a small portion of end 22a of lacerated tendon 22 and to effectively isolate end 22a of a lacerated tendon 22 from closely adjacent body tissues (not expressly shown). Clamp assembly 30 and manipulator 100 cooperate with each other to prevent repetitive grasping and manipulation of lacerated ends 22a and 22b of tendon 22 during placement of sutures 24 and 26 therein.

Various features of the present invention will be described with respect to placing sutures 24 and 26 in lacerated ends 22a and 22b of tendon 22 as shown in FIGS. 4A–4D, 5 and 6. Sutures 24 and 26 are preferably identical and include respective straight needles 28 and 29 disposed in opposite ends thereof. See FIG. 4C. Therefore, only suture 24 will be described in detail. Sutures 24 and 26 may be either type 4-0 or 3-0.

Using conventional surgical techniques, approximately at least one centimeter (ten millimeters) of lacerated end 22a will be exposed or made available for repair. Manipulator 100 is used to hold clamp assembly 30 in its first, open position. Lacerated end 22a is gently but firmly placed within channel 40 and engaged with spikes 46. Spikes 46 penetrate lacerated end 22a to help secure lacerated end 22a within channel 40. Manipulator 100 may then be used to close clamp assembly 30 as shown in FIG. 4B.

Clamp assembly 30 is preferably engaged with lacerated end 22a such that only a relatively small, damaged portion 23 of lacerated end 22a will extend from channels 38 and 40. End 56 of first jaw 32 and end 58 of second jaw 34 immediately adjacent to damaged portion 23 preferably form a smooth, flat surface. Ends 56 and 58 of clamp assembly 30 serves as a cutting guide to allow efficient, accurate trimming, when required, of lacerated tendon end 22a to remove any oblique, jagged or crushed portions. Damaged portion 23 of lacerated end 22a may be trimmed with a razor or scalpel using ends 56 and 58 as a cutting guide. As a result, a generally smooth, perpendicular surface 25 on lacerated end 22a will be exposed at the end of clamp assembly 30 corresponding with ends 56 and 58 of jaws 32 and 34. See FIG. 4C.

Jaws 32 and 34 cooperate with each other to firmly grasp lacerated end 22a during the trimming process. A clamp assembly having a cutting guide formed in accordance with teaching of the present invention will generally eliminate many of the frustrations encountered in repairing tendons and ligaments with oblique, jagged, or crushed ends.

After clamp assembly 30 has been satisfactorily engaged with lacerated end 22a of tendon 22 as shown in FIG. 4B and damaged portion 23 removed, manipulator 100 may be rotated or pivoted from its second position to its third position as shown in FIGS. 3 and 4C. Clamp assembly 30 may be positioned to allow better access for placement of sutures 24 and 26 within lacerated end 22a of tendon 22 when manipulator 100 is in its third position.

Holes 71, 72, 73 and 74 cooperate with each other to guide movement of needles 28 and 29 through lacerated end 22a of tendon 22. For the embodiment of the present invention as represented by clamp assembly 30, each needle 28 and 29 will pass two or three times through lacerated end 22a of tendon 22. As desired by the surgeon, either needle 28 or needle 29 will first be inserted through hole 73. After this first pass of the associated suture 24 or 26, each needle 28 and 29 will then pass through holes 71 and 72.

A clamp assembly incorporating teachings of the present invention will preferably result in each suture strand 24a, 24b, 26a and 26b exiting from different quadrants of lacerated end 22a of tendon 22. See FIG. 5. For some applications, color coding and/or numbers (not expressly shown) may be placed on the exterior of clamp assembly 30 adjacent to respective holes 71, 72, 73 and 74 to provide directions for inserting needles 28 and 29 in the desired sequence. However, a clamp assembly incorporating teachings of the present invention may be satisfactorily used without such color coding or numbers.

With the last pass of respective needles 28 and 29, the respective ends of suture 24 will exit from surface 25 lacerated end 22a of tendon 22. Needles 28 and 29 may then be removed from suture 24 leaving sutures strands 24a and 24b extending from respective quadrants of lacerated end 22a. Suture 26 may be placed within lacerated end 22a using the guide path defined in part by slots 62 and 64 and substantially the same techniques as previously described for suture 24.

After sutures 24 and 26 have been satisfactorily placed within lacerated end 22a of tendon 22, manipulator 100 may be returned to its second position such as shown in FIGS. 2 and 4B. Clamp assembly 30 may then be opened by placing manipulator 100 in its first position as shown in FIGS. 1 and 4D to allow removal of lacerated end 22a of tendon 24 with suture strands 24a, 24b, 26a and 26b extending longitudinally from surface 25.

After sutures 24 and 26 have been properly placed within lacerated end 22a of tendon 22, tendon repairing system 20 may then be applied to lacerated end 22b of tendon 22. Respective sutures 24 and 26 may be placed within lacerated end 22b of tendon 22 using similar procedures and techniques as previously described with respect to lacerated end 22a. For some surgical procedures, tendon repairing system 20 may be discarded after placement of sutures 24 and 26 in lacerated end 22a of tendon 22 and a new tendon repairing system 20 may then be used to place respective suture threads 24 and 26 within lacerated end 22b of tendon 22.

Once suture placement has been completed in both lacerated ends 22a and 22b, respective suture strands 24a, 24b, 26a and 26b may be matched and tied using typical suture tying procedures associated with tendon and/or ligament repair. Because each suture strand 24a 24b 26a and 26b exits from a respective quadrant of the tendon ends 22a and 22b, the matching-up of suture strands 24a, 24b, 26a and 26b is straightforward. For some applications, color-coding of sutures 24 and 26 may be incorporated to further assist in matching suture strands 24a, 24b, 26a and 26b.

After the suture repair is completed, the remainder of the operation, splinting and rehabilitation proceeds according to appropriate techniques for the associated tendon, ligament or fibrous body tissue.

The various components of tendon repairing system 20 may be manufactured from a wide variety of materials. For some applications, the various components associated with clamp assembly 30 and manipulator 100 may be formed from plastic type materials using injection molding techniques. Examples of such plastic materials include polypropylene and acrylic compounds. Other types of polymeric materials may be satisfactorily used to form tendon repairing system 20. Typically the materials and manufacturing procedures to form tendon repairing system 20 will be selected to reduce manufacturing costs such that each tendon repairing system 20 may be disposed of or discarded following use. For some applications, tendon repairing system 20 may be formed from various metal alloys and/or composite materials particularly for use in surgical procedures requiring relatively high strength and/or durability. Appropriately sized sutures and needles may also be packaged with each tendon repairing system along with appropriate instructions.

A clamp assembly incorporating teachings of the present invention may have jaws and respective channels with configurations other than the configuration of channels 38 and 40. Ribs 42 and 44 may or may not be provided in such channels. For example, the configuration and dimensions of such channels may be selected to correspond with the dimensions and configuration of a specific ligament such as a large ligament in a patient's leg or arm. For other applications, such channels may cooperate with each other to form a passageway extending through the associated clamp assembly having a generally circular cross-section, rectangular cross-section or square cross-section as appropriate for each specific surgical procedure and type of fibrous body tissue which will be disposed therein. Also, the dimensions and configuration of one channel may be different from the dimensions and configuration of the associated channel. Selection of the dimensions and configuration of a clamp assembly, associated jaws and channels may be made in accordance with teachings of the present invention to allow efficient and reproducible surgical repairs of lacerated tendons, ligaments and similar types of fibrous body tissue.

A clamp assembly for releasably holding the lacerated end of a tendon or ligament in accordance with teachings of the present invention may have jaws with configurations other than the generally box-type configurations of jaws 32 and 34. For some applications, each jaw may have a configuration corresponding generally with one half of a cylinder. When such jaws are in their closed position, they will cooperate with each other to form a complete cylinder. For other applications, a clamp assembly may be provided with a pair of jaws having non-symmetrical configurations.

A clamp assembly for releasably holding the lacerated end of a tendon or ligament in accordance with teachings of the present invention may have various types of hinge mechanisms other than active hinge 36. For some applications, the lacerated end of a tendon or ligament may be releasably engaged by a clamp assembly having a pair of jaws which do not include a hinge disposed therebetween.

A clamp assembly and manipulator for releasably holding the lacerated end of a tendon or ligament in accordance with teachings of the present invention may have various locking mechanisms for releasably securing the associated clamp assembly in its second, closed position when the lacerated end of a tendon or ligament is disposed therein. For some applications, the locking mechanism may include one or more flexible snaps or collets attached to selected portions of the associated clamp assembly. For other applications, the associated manipulator may include one or more detentes, flexible collets and/or snaps to releasably secure the respective clamp assembly in its second, closed position. A wide variety of well known locking mechanisms may be satisfactorily used with the present invention. The present invention is not limited to use with collets 52 and 53 and recesses 54.

The present invention is not limited to suture guide paths having holes and slots with configurations as shown in this application. A wide variety of configurations and dimensions may be satisfactorily used as long as one portion of the suture guide path will guide movement of a needle or needles and another portion will only allow movement of the suture therethrough.

Although the present invention and its advantages have been described in detail, it should be understood that various changes, substitutions and alterations can be made herein without departing from the spirit and scope of the invention as defined by the following claims.

What is claimed is:

1. A tendon suture-repair device comprising:
   an enclosure for releasably holding a lacerated end of a tendon within a channel having a longitudinal axis and a generally oval shaped cross section to accommodate the tendon;
   the enclosure having at least one slot and at least one hole which forms an acute angle with respect to said longitudinal axis for guiding placement of a suture strand exiting from the lacerated end of the tendon; and
   a manipulator for opening and closing portions of the enclosure.

2. A tendon repair system comprising:
   a clamp assembly having a longitudinal axis for releasably holding a lacerated end of a tendon;
   at least one suture guide path defined in part by a slot formed in the clamp assembly for placement of a suture in the lacerated end and a hole which forms an acute angle with respect to said longitudinal axis to direct placement of a suture strand exiting from the lacerated end of the tendon; and
   a manipulator for opening and closing the clamp assembly.

3. The tendon repair system of claim 2 wherein the clamp assembly further comprises:
   a pair of jaws with each jaw having a channel formed therein and extending generally longitudinally therethrough;
   the clamp assembly having a first position with the jaws spaced from each other to allow placement of the lacerated end of the tendon within one of the channels; and
   the clamp assembly having a second position with the jaws disposed immediately adjacent to each other to releasably hold the lacerated end within the channels.

4. The tendon repair system of claim 2 wherein the clamp assembly further comprises:
   a pair of jaws with each jaw having a channel formed therein and extending longitudinally therethrough; and
   at least one of the channels having a plurality of spikes disposed therein for engagement with the lacerated end.

5. The tendon repair system of claim 2 wherein the clamp assembly further comprises:
   a pair of jaws with a hinge attached thereto and extending along one side of the clamp assembly; and
   the hinge cooperating with the manipulator for opening and closing the clamp assembly.

6. The tendon repair system of claim 2 wherein the clamp assembly further comprises:
   a pair of jaws with each jaw having a channel formed therein and extending longitudinally therethrough;
   each channel having a cross section corresponding approximately with one half of an oval; and the channels cooperating with each other to form a passageway having a generally oval shaped cross section extending longitudinally through the clamp assembly when the clamp assembly is in its closed position.

7. The tendon repair system of claim 2 further comprising:
a first jaw and a second jaw which cooperate with each other to form a longitudinal passageway for releasably holding the lacerated end of the tendon when the clamp assembly is closed; and
a locking mechanism for releasably engaging the first jaw with the second jaw when the clamp assembly is closed.

8. The tendon repair system of claim 7 wherein the locking mechanism further comprises:
a pair of flexible collets attached to and extending from the first jaw; and
a pair of recesses formed in the second jaw aligned with and sized to respectively receive one of the collets.

9. The tendon repair system of claim 2 further comprising:
a longitudinal passageway for releasably holding the lacerated end of the tendon when the clamp assembly is closed;
the manipulator having a position extending generally normal to the longitudinal passageway during opening and closing of the clamp assembly; and
the manipulator having another position extending generally parallel with the longitudinal passageway during placement of the suture in the lacerated end.

10. A suture repair device comprising:
a clamp assembly having a longitudinal passageway formed therein for releasably holding a lacerated end of a fibrous body tissue;
a first suture guide path defined in part by at least one hole which forms an acute angle with respect to said longitudinal passageway and one slot formed in the clamp assembly for use in directing placement of a first suture strand exiting from the lacerated end; and
a second suture guide path defined in part by at least one hole and one slot formed in the clamp assembly for use in directing placement of a second suture strand through said fibrous body tissue.

11. The suture repair device of claim 10 wherein the first suture guide path further comprises:
a first slot and a second slot formed in the clamp assembly;
the first slot and the second slot generally aligned with each other and intersecting the longitudinal passageway; and
each slot having a generally trapezoidal configuration.

12. The suture repair device of claim 10 further comprising the longitudinal passageway sized to releasably hold fibrous body tissue selected from the group consisting of a tendon and a ligament.

13. The suture repair device of claim 10 further comprising:
the clamp assembly having a first jaw and a second jaw;
the manipulator having a first arm and a second arm;
the first arm having a first segment rotatably attached to the first jaw; and
the first arm having a second segment rotatably attached to both the first segment and the second arm whereby movement of the first segment and the second segment of the first arm relative to each other and relative to the second arm will open and close the clamp assembly.

14. A suture repair device comprising:
a clamp assembly having a longitudinal passageway formed therein for releasably holding a lacerated end of a fibrous body tissue;
at least one suture guide path formed in the clamp assembly for directing placement of a suture in the lacerated end;
a manipulator for opening and closing the clamp assembly;
the manipulator aligned generally normal to the longitudinal passageway while opening and closing the clamp assembly; and
the manipulator aligned generally parallel with the longitudinal passageway when the clamp assembly is in the closed position during placement of at least one suture in the lacerated end.

15. Apparatus for releasably holding one end of a lacerated fibrous body tissue and guiding placement of at least one suture therethrough comprising:
a clamp assembly having a longitudinal passageway formed therein for releasably holding the lacerated end of the fibrous body tissue;
at least one suture guide path formed in the clamp assembly for placement of a suture in the lacerated end;
a manipulator for opening and closing the clamp assembly; and
the clamp assembly having a first jaw and a second jaw;
the manipulator having a first arm and a second arm; and
one end of the first arm pivotally attached to the first jaw and one end of the second arm pivotally attached to the second jaw whereby the manipulator is moved from a position extending generally normal to the longitudinal passageway to another position extending generally parallel with the longitudinal passageway when said clamp assembly is in the closed position.

16. Apparatus for releasably holding one end of a lacerated fibrous body tissue and guiding placement of at least one suture therethrough comprising:
a clamp assembly having a longitudinal passageway formed therein for releasably holding the lacerated end of the fibrous body tissue;
at least one suture path formed in the clamp assembly for placement of a suture in the lacerated end;
a manipulator for opening and closing the clamp assembly;
the longitudinal passageway having a longitudinal axis extending therethrough;
a second suture guide path formed in the clamp assembly for use in directing placement of a second suture in the lacerated end; and
said at least one suture guide path intersecting with the second suture guide path at an angle of approximately forty-five degrees with respect to the longitudinal center line of the longitudinal passageway.

17. A suture repair device comprising:
a clamp assembly having a longitudinal passageway formed therein for releasably holding a lacerated end of a fibrous body tissue;
at least a first suture guide path formed in the clamp assembly for use in directing placement of at least one suture strand exiting from the lacerated end;
the first suture guide path defined in part by a first slot and a second slot formed in the clamp assembly;

the first slot and the second slot generally diametrically aligned with each other and extending in the direction of the longitudinal passageway;

a plurality of holes extending through the first slot and the second slot and the holes sized to allow a needle to pass therethrough; and the dimensions of the first slot and the second slot selected to allow movement of the suture therethrough and to prevent movement of the needle therethrough.

18. The suture repair device of claim 17 further comprising;

at least a second suture guide path formed in the clamp assembly for use in directing placement of a second suture strand exiting from the lacerated end of the fibrous body tissue;

the second suture guide path having a configuration corresponding generally with the first suture guide path; and the second suture guide path intersecting the longitudinal passageway at an angle offset from the first suture guide path.

19. A tendon repair system comprising:

a clamp assembly for releasably holding a lacerated end of a fibrous body tissue;

the clamp assembly having a pair of jaws with each jaw including a channel extending longitudinally therethrough;

at least one of the channels having a plurality of spikes disposed therein for engagement with the lacerated end;

a manipulator for opening and closing the clamp assembly;

the manipulator having a position extending generally normal to the longitudinal passageway; and the manipulator having another position extending generally parallel with the longitudinal passageway.

20. Apparatus for releasably holding one end of a lacerated fibrous body tissue, trimming the lacerated end and guiding placement of at least one suture therethrough comprising:

a clamp assembly having a generally longitudinal passageway formed therein for releasably holding the lacerated end of the fibrous body tissue;

the longitudinal passageway having a generally oval shaped cross-section sized to accommodate the fibrous body tissue;

a plurality of spikes disposed within the longitudinal channel for engagement with the fibrous body tissue;

a manipulator for opening and closing the clamp assembly; and one end of the clamp assembly having a generally smooth, flat surface which serves as a cutting guide to allow efficient, accurate, trimming of the lacerated end of the fibrous body tissue to remove any oblique, jagged or crushed portions.

* * * * *